US006277617B1

(12) United States Patent
Bott et al.

(10) Patent No.: US 6,277,617 B1
(45) Date of Patent: *Aug. 21, 2001

(54) CHEMICALLY MODIFIED ENZYMES

(75) Inventors: Richard R. Bott, Burlingame; Thomas P. Graycar, Pacifica, both of CA (US); J. Bryan Jones, 1275 Seaforth Crescent, Lakefield (CA), KOL 2HO; Colin Mitchinson, Half Moon Bay, CA (US)

(73) Assignees: Genencor International, Inc., Rochester, NY (US); J. Bryan Jones, Lakefield (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/978,509

(22) Filed: Nov. 25, 1997

Related U.S. Application Data

(63) Continuation-in-part of application No. 08/756,664, filed on Nov. 26, 1996, now abandoned.

(51) Int. Cl.$^7$ .................................................. A61K 38/48

(52) U.S. Cl. ........................ 435/219; 435/221; 435/69.1
(58) Field of Search ................................... 435/219, 221, 435/69.1; 510/530; 514/2; 530/402, 404, 405, 406

(56) References Cited

U.S. PATENT DOCUMENTS 5,316,935   5/1994   Arnold et al. ........................ 435/222

FOREIGN PATENT DOCUMENTS

| 0 328 229 A1 | 8/1989 | (EP) . |
|---|---|---|
| 91/16423 | 10/1991 | (WO) . |
| 96/27671 | 9/1996 | (WO) . |

OTHER PUBLICATIONS

Berglund et al., "Altering the Specificity of Subsilisin B. Lentus by Combining Site–Directed Mutagenesis and Chemical Modification," *Bioorganic & Mechanical Chemistry Letters*, 6:2507–2512 (1996).
Bech et al., "Chemical Modifications of a Cysteinyl Residue Introduced in the Binding Site of Carboxypeptidase Y by Site–Directed Mutagenesis," *Carlsberg Res. Commun.*, 53:381–393 (1988).
Wynn et al., "Chemical Modification of Protein Thiols: Formation of Mixed Disulfides," *Methods in Enzymology*, 251:351–356(1995).
Bonneau et al., Alteration of the Specificity of Subtilisin BPN' by Site Directed Mutagenesis in Its $S_1$ and $S_1$' Binding Sites, *J. Am. Chem. Soc.*, 113:1026–1030 (1991).

Gloss et al., "Examining the Structural and Chemical Flexibility of the Active Site Base, Lys–258, of *Escherichia coli* Aspartate Aminotransferase by Replacement with Unnatural Amino Acids," *Biochemistry*, 34:12323–12332 (1995).
Wynn et al., "Mobile Unnatural Amino Acid Side Chains in the Core of Staphylococcal Nuclease," *Protein Science*, 5:1026–1031 (1996).
Berglund et al., "Chemical Modification of Cysteine Mutants of Subtilisin *Bacillus Lentus* Can Create Better Catalysts Than The Wild–Type Enzyme," *J. Am. Chem. Soc.*, 119:5265–5266 (1997).
Gron et al., "A Highly Active and Oxidation–Resistant Subtilisin–Like Enzyme Produced by a Combination of Site–Directed Mutagenesis and Chemical Modification," *Eur. J. Biochem.*, 194:897–901 (1990).
Bech et al., "Significance of Hydrophobic $S_4$–$P_4$ Interactions in Subtilisin 309 from *Bacillus Lentus*," *Biochemistry*, 32:2847–2852 (1993).
Wynn et al,. "Unnatural Amino Acid Packing Mutants of *Escherichia Coli* Thioredoxin Produced by Combined Mutagenesis/Chemical Modification Techniques," *Protein Science*, 2:395–403 (1993).
Wynn et al., "Comparison of Straight Chain and Cyclic Unnatural Amino Acids Embedded in the Core of Staphylococcal Nuclease," *Protein Science*, 6:1621–1626 (1997).
Kawase et al., "Effect of Chemical Modification of Tyrosine Residues on Activities of Bacterial Lipase," *Journal of Fermentation and Bioengineering*, 72:317–319 (1991).
Raia et al., "Activation of *Sulfolobus Solfataricus* Alcohol Dehydrogenase by Modification of Cysteine Residue 38 with Iodoacetic Acid," *Biochemistry*, 35:638–647 (1996).

(List continued on next page.)

*Primary Examiner*—Jean C. Witz
(74) *Attorney, Agent, or Firm*—McCutchen, Doyle, Brown & Enerson, LLP

(57) ABSTRACT

Modified enzymes are provided in which at least one amino acid, such as asparagine, leucine, methionine or serine, of an enzyme is replaced with a cysteine and the thiol hydrogen is replaced with a substituent group providing a thiol side chain selected from the group consisting of:

a) —$SR^1R^2$, wherein $R^1$ is an alkyl and $R^2$ is a charged or polar moiety;
b) —$SR^3$, wherein $R^3$ is a substituted or unsubstituted phenyl;
c) —$SR^4$, wherein $R^4$ is substituted or unsubstituted cyclohexyl;
d) —$SR^5$, wherein $R^5$ is $C_{10}$–$C_{15}$ alkyl; and
e) —$SR^6$ wherein $R^6$ is a $C_{1-6}$ alkyl.

Also, methods of producing the modified enzymes are provided, as well as detergent and feed additives and a composition for the treatment of a textile. A method for using the modified enzymes in organic synthesis is additionally provided. Further, modified enzymes having improved activity, altered pH profile and/or wash performance are provided.

39 Claims, 3 Drawing Sheets

OTHER PUBLICATIONS

Ramachandran et al., "Stabilization of Barstar by Chemical Modification of the Buried Cysteines," *Biochemistry*, 35:8776–8785 (1996).

Davies et al., "A Semisynthetic Metalloenzyme Based on a Protein Cavity That Catalyzes the Enantiosleective Hydrolysis of Ester and Amide Substrates," *J. Am. Chem. Soc.*, 119:11643–11652 (1997).

Polgar et al., "A New Enzyme Containing a Synthetically Formed Active Site. Thiol–Subtilisin," *Journal of American Chemical Society*, 88:3153–3154 (1996).

Stewart et al., "Catalytic Oxidation of Dithiols by a Semisynthetic Enzyme," *J. Am. Chem. Soc.*, 108:3480–3483 (1986).

Radziejewski et al., "Catalysis of N–Alkyl–1,4–Dihydronicotinamide Oxidation by a Flavopapain: Rapid Reaction in All Catalytic Steps," *J. Am. Chem. Soc.*, 107:3352–3354 (1985).

Hilvert et al., "A Highly Active Thermophilic Semisynthetic Flavoenzyme," *J. Am. Chem. Soc.*, 110:682–689 (1988).

Hilvert et al., "New Semisynthetic Flavoenzymes Based on a Tetrameric Protein Template, Glyceraldehyde–3–Phosphate Dehydrogenase," *J. Am. Chem. Soc.*, 107:5805–5806 (1985).

Rokita et al., "Synthesis and Characterization of a New Semisynthetic Enzyme, Flavolysozyme," *J. Am. Chem. Soc.*, 108:4984–4987 (1986).

Kokubo et al., "Flavohemoglobin: A Semisynthetic Hydroxylase Acting in the Absence of Reductase," *J. Am. Chem. Soc.*, 109:606–607 (1987).

Suckling et al., "Carbon–Carbon Bond Formation Mediated by Papain Chemically Modified by Thiazolium Salts," *Bioorganic & Medicinal Chemistry Letters*, 3:531–534 (1993).

Di Bello, "Total Synthesis of Proteins by Chemical Methods: The Horse Heart Cytochrome C Example," *Gazzetta Chimica Italiana*, 126:189–197 (1996).

O'Connor et al., "Probing an Acyl Enzyme of Selenosubtilisin by Raman Spectroscopy," *J. Am. Chem. Soc.*, 118: 239–240 (1996).

Peterson et al., "Nonessential Active Site Residues Modulate Selenosubtilisin's Kinetic Mechanism," *Biochemistry*, 34:6616–6620 (1995).

Bell et al., "Kinetic Studies on the Peroxidase Activity of Selenosubtilisin," *Biochemistry*, 32:3754–3762 (1993).

Peterson et al., "Selenosubtilisin's Peroxidase Activity Does Not Require an Intact Oxyanion Hole," *Tetrahedron*, 53:12311–12317 (1997).

Wu et al., "Conversion of a Protease into an Acyl Transferase: Selenolsubtilisin," *J. Am. Chem. Soc.*, 111:4514–4515 (1989).

House et al., "$^1$H NMR Spectroscopic Studies of Selenosubtilisin," *Biochemistry*, 32:3468–3473 (1993).

Valenzuela et al., "Kinetic Properties of Succinylated and Ethylenediamine–Amidated §–Chymotrypsins," *Biochim. Biophys. Acta*, 250:538–548 (1971).

Siddiqui et al., "Arthrobacter D–Xylose Isomerase: Chemical Modification of Carboxy Groups and Protein Engineering Of pH Optimum," *Biochem. J.*, 295:68–691 (1993).

Kuang et al., "Enantioselective Reductive Amination of β–Keto Acids to β–Amino Acids by a Pyridoxamine Cofactor in A Protein Cavity," *J. Am. Chem. Soc.*, 118:10702–10706 (1996).

West et al., "Enzymes as Synthetic Catalysts: Mechanistic and Active–Site Considerations of Natural and Modified Chymotrypsin," *J. Am. Chem. Soc.*, 112:5313–5320 (1990).

White et al., "Sequential Site–Directed Mutagenesis and Chemical Modification to Convert the Active Site Arginine 292 Of Aspartate Aminotransferase to Homoarginine," *Journal of the American Chemical Society*, 114:292–293 (1992).

Engler et al., "Critical Functional Requirement for the Guanidinium Group of the Arginine 41 Side Chain of Human Epidermal Growth Factor as Revealed by Mutagenic Inactivation and Chemical Reactivation," *The Journal of Biological Chemistry*, 267:2274–2281 (1992).

Planas et al., "Reengineering the Catalytic Lysine of Aspartate Aminotransferase by Chemical Elaboration of a Genetically Introduced Cysteine," *Biochemistry*, 30:8268–8276 (1991).

Smith et al., "An Engineered Change in Substrate Specificity of Ribulosebisphosphate Carboxylase/Oxygenase," *The Journal of Biological Chemistry*, 265:1243–1245 (1990).

Smith et al., "Subtle Alteration of the Active Site of Ribulose Bisphosphate Carboxylase/Oxygenase by Concerted Site–Directed Mutagenesis and Chemical Modification," *Biochemical and Biophysical Research Communications*, 152:579–584 (1988).

Smith et al., "Restoration of Activity to Catalytically Deficient Mutants of Ribulosebisphosphate Carboxylase/Oxygenase by Aminoethylation," *The Journal of Biological Chemistry*, 263:4921–4925 (1988).

Kanaya et al., "Role of Cysteine Residues in Ribonuclease H from *Escherichia coli*," *Biochem. J.*, 271:59–66 (1990).

Xu et al., "Amino Acids Lining the Channel of the γ–Am inobutyric Acid Type A Receptor Identified by Cysteine Substitution," *The Journal of Biological Chemistry*, 268:21505–21508 (1993).

Svensson et al., "Mapping the Folding Intermediate of Human Carbonic Anhydrase II. Probing Substructure by Chemical Reactivity and Spin and Fluorescence Labeling of Engineered Cysteine Residues," *Biochemistry*, 34:8606–8620 (1995).

Akabas et al., "Acetylcholine Receptor Channel Structure Probed in Cysteine–Substitution Mutants," *Science*, 258:307–310 (1992).

Liu et al., "Site–Directed Fluorescence Labeling of P–Glycoprotein on Cysteine Residues in the Nucleotide Binding Domains," *Biochemistry*, 35:11865–11873 (1996).

Frillingos et al., "Cysteine–Scanning Mutagenesis of Helix II and Flanking Hydrophilic Domains in the Lactose Permease of *Escherichia coli*," *Biochemistry*, 36:269–273 (1997).

Kirley, "Reduction and Fluorescent Labeling of Cyst(e)ine––Containing Proteins for Subsequent Structural Analyses," *Analytical Biochemistry*, 180:231–236 (1989).

Buckwalter et al., "Improvement in the Solution Stability of Porcine Somatotropin by Chemical Modification of Cysteine Residues," *J. Agric. Food Chem.*, 40:356–362 (1992).

Nishimura et al., "Reversible Modification of the Sulfhydryl Groups of *Escherichia coli* Succinic Thiokinase with Methanethiolating Reagents, 5,5'–Dithio–bis(2–Nitrobenzoic Acid), p–Hydroxymercuribenzoate, and Ethylmercurithiosalicylate," *Archives of Biochemistry and Biophysics*, 170:461–467 (1975).

Lewis et al., "Determination of Interactive Thiol Ionizations in Bovine Serum Albumin, Glutathione, and Other Thiols by Potentiometric Difference Titration," *Biochemistry*, 19:6129–6137 (1980).

Worku et al., "Identification of Histidyl and Cysteinyl Residues Essential for Catalysis by 5'–Nucleotidase," *FEBS Letters*, 167:235–240 (1984).

Smith et al., "Chemical Modification of Active Site Residues in γ–Glutamyl Transpeptidase," *The Journal of Biological Chemistry*, 270:12476–12480 (1995).

Smith et al., "Nonessentiality of the Active Sulfhydryl Group of Rabbit Muscle Creatine Kinase," *The Journal of Biological Chemistry*, 249:3317–3318 (1974).

Roberts et al., "Reactivity of Small Thiolate Anions and Cysteine–25 in Papain Toward Methyl Methanethiosulfonate," *Biochemistry*, 25:5595–5601 (1986).

Pardo et al., "Cysteine 532 and Cysteine 545 Are theN–Ethylmaleimide–Reactive Residues of the Neurospora Plasma Membrane $H^+$–ATPase," *The Journal of Biological Chemistry*, 264:9373–9379 (1989).

Hempel et al., "Selective Chemical Modification of Human Liver Aldehyde Dehydrogenases $E_1$ and $E_2$ by Iodoacetamide," *The Journal of Biological Chemistry*, 256:10889–10896 (1981).

Daly et al., "Formation of Mixed Disulfide Adducts at Cysteine–281 of the Lactose Repressoree Protein Affects Operator And Inducer Binding Parameters," *Biochemistry*, 25:5468–5474 (1986).

Bodwell et al., "Sulfhydryl–Modifying Reagents Reversibly Inhibit Binding of Glucocorticoid–Receptor Complexes to DNA–Cellulose," *Biochemistry*, 23:1392–1398 (1984).

Alvear et al., "Inactivation of Chicken Liver Mevalonate 5–Diphosphate Decarboxylase by Sulfhydryl–Directed Reagents: Evidence of a Functional Dithiol," *Biochimica et Biophysica Acta*, 994:7–11 (1989).

Miller et al., "Peroxide Modification of Monoalkylated Glutathione Reductase," *The Journal of Biological Chemistry*, 266:19342–19360 (1991).

Soper et al., "Effects of Substrates on the Selective Modification of the Cysteinyl Residues of D–Amino Acid Transaminase," *The Journal of Biological Chemistry*, 254:10901–10905 (1979).

Stauffer et al., "Electrostatic Potential of the Acetylcholine Binding Sites in the Nicotinic Receptor Probed by Reactions Of Binding–Site Cysteines with Charged Methanethiosulfonates," *Biochemistry*, 33:6840–6849 (1994).

Nakayama et al., "Chemical Modification of Cysteinyl, Lysyl and Histidyl Residues of Mouse Liver 17β–Hydroxysteroid Dehydrogenase," *Biochimica et Biophysica Acta*, 1120:144–150 (1992).

Huang et al., "Improving the Activity of Immobilized Subtilisin by Site–Specific Attachment to Surfaces," *Anal. Chem.*, 69:4601–4607 (1997).

Brocklehurst, "Specific Covalent Modification of Thiols: Applications in the Study of Enzymes and Other Biomolecules," *Int. J. Biochem.*, 10:259–274 (1979).

Bruice et al., "Novel Alkyl Alkanethiolsulfonate Sulfhydryl Reagents. Modification of Derivatives of L–Cysteine," *Journal of Protein Chemistry*, 1:47–58 (1982).

Smith et al., "Simple Alkanethiol Groups for Temporary Blocking of Sulfhydryl Groups of Enzymes," *Biochemistry*, 14:766–771 (1975).

Polgar, "Spectrophotometric Determination of Mercaptide Ion, an Activated Form of SH–Group in Thiol Enzymes," *FEBS Letters*, 38:187–190 (1974).

Konigsberg, "Reduction of Disulfide Bonds in Proteins with Dithiothreitol," *Methods in Enzymology*, 25:185–188 (1972).

Kenyon et al., "Novel Sulfhydryl Reagents," *Methods Enzymol.*, 47:407–430 (1977).

Kluger et al., "Amino Group Reactions of the Sulfhydryl Reagent Methyl Methanesulfonothioate. Inactivation of D–3–hydroxybutyrate Dehydrogenase and Reaction with Amines in Water," *Can . J. Biochem.*, 58:629–632 (1980).

Kaiser, "Catalytic Activity of Enzymes Altered at Their Active Sites," *Angew. Chem. Int. Ed. Engl.*, 27:913–922 (1988).

Bech et al., "Chemical Modifications of a Cysteinyl Residue Introduced in the Binding Site of Carboxypeptidase Y by Site–Directed Mutagenesis," *Carlsberg Research Communications*, vol. 53, pp. 381–393 (1988).

Berglund et al., "Chemical Modification of Cysteine Mutants of Subtilisin *Bacillus lentus* can Create Better Catalysts than the Wild–Type Enzyme," *Journal of the American Chemical Society*, vol. 119., pp. 5265–5266 (1997).

Berglund et al., "Altering the Specificity of Subtilisin *B. lentus* by Combining Site–Directed Mutagenesis and Chemical Modification," *Bioorganic & Mechanical Chemistry Letters*, vol. 6, No. 21, pp. 2507–2512 (1996).

Bonneau et al., "Alteration of the Specificity of Subtilisin BPN' by Site–Directed Mutagenesis in its $S_1$ and $S_1$'Binding Sites," *Journal of the American Chemical Society*, vol. 113, pp. 1026–1030 (1991).

Gloss et al., "Examining the Structural and Chemistry Flexibility of the Active Site Base, Lys–258, of *Escherichia coli* Aspartate Aminotransferase by Replacement with Unnatural Amino Acids," *Biochemistry*, vol. 34, pp. 12323–12332 (1995).

Wynn et al., "Chemistry Modification of Protein Thiols: Formation of Mixed Disulfides," *Methods in Enzymology*, vol. 251, pp. 351–356 (1995).

Wynn et al., "Mobile Unnatural Amino Acid Side Chains in the Core of Staphylococcal Nuclease," *Protein Science*, vol. 5, pp. 1026–1031 (1996).

Neet, K.E. and Koshland, D.E., "The Conversion of Serine at the Active Site of Subtilisin to Cysteine: A 'Chemical Mutation,'" *Proc. Nat. Acad. Sci. USA*, 56(5):1606–1611.

Betzel et al. "Crystal Structure or the Alkaline Proteinase Savinase (TM) from *Bacillus lentus* at 1.4 angstrom Resolution," J. Mol. Biol. (1992) 223:427–445.*

Huang et al. "Improving the Activity of Immobilized Subtilisin by Site–Specific Attachment to Surfaces," Anal. Chem. (1997) 89: 46–1–7.*

* cited by examiner

CHEMICALLY MODIFIED ENZYMES

CROSS-REFERENCE TO RELATED APPLICATIONS

This application is a continuation-in-part of U.S. application Ser. No. 08/756,664 filed Nov. 26, 1996 now ABN, and which is incorporated herein by reference in its entirety.

BACKGROUND OF THE INVENTION

Modifying enzyme properties by site-directed mutagenesis has been limited to natural amino acid replacements, although molecular biological strategies for overcoming this restriction have recently been derived (Cornish, V. W. et al. (1995) *Angew. Chem.*, Int. Ed. Engl. 34:621). However, the latter procedures are not generally easy to apply in most laboratories. In contrast, controlled chemical modification of enzymes offers broad potential for facile and flexible modification of enzyme structure, thereby opening up extensive possibilities for controlled tailoring of enzyme specificity.

Changing enzyme properties by chemical modification has been explored previously, with the first report being in 1966 by the groups of Bender (Polgar, L. et al. (1966) J. Am. Chem. Soc. 88:3153) and Koshland (Neet, K. E. et al. (1966) *Proc. Natl. Acad. Sci. USA* 56:1606), who created a thiol-subtilisin by chemical transformation ($CH_2OH \rightarrow CH_2SH$) of the active site serine residue of subtilisin BPN' to cysteine. Interest in chemically produced artificial enzymes, including some with synthetic potential, was renewed by Wu, Z. -P. et al. (1989) *J. Am. Chem. Soc.* 111:4514; Bell, I. M. et al. (1993) *Biochemistry* 32:3754 and Peterson, E. B. et al. (1995) *Biochemistry* 34:6616, and more recently by Suckling, C. J. et al. (1993) *Bioorg. Med. Chem. Lett.* 3:531.

Enzymes are now widely accepted as useful catalysts in organic synthesis. However, natural, wild-type, enzymes can never hope to accept all structures of synthetic chemical interest, nor always to transform them stereospecifically into the desired enantiomerically pure materials needed for synthesis. This potential limitation on the synthetic applicabilities of enzymes has been recognized, and some progress has been made in to altering their specificities in a controlled manner using the site-directed and random mutagenesis techniques of protein engineering. However, modifying enzyme properties by protein engineering is limited to making natural amino acid replacements, and molecular biological methods devised to overcome this restriction are not readily amenable to routine application or large scale synthesis. The generation of new specificities or activities obtained by chemical modification of enzymes has intrigued chemists for many years, and continues to do so. The inventors have adopted the combined site-directed mutagenesis-chemical modification strategy since it offers virtually unlimited possibilities for creating new structural environments at any amino acid location.

U.S. Pat. No. 5,208,158 describes chemically modified detergent enzymes wherein one or more methionines have been mutated into cysteines. The cysteines are subsequently modified in order to confer upon the enzyme improved stability towards oxidative agents. The claimed chemical modification is the replacement of the thiol hydrogen with a $C_{1-6}$ alkyl.

Although U.S. Pat. No. 5,208,158 has described altering the oxidative stability of an enzyme, it would also be desirable to develop one or more enzymes with altered properties such as activity, nucleophile specificity, substrate specificity, stereoselectivity, thermal stability, pH activity profile and surface binding properties for use in, for example, detergents or organic synthesis.

SUMMARY OF THE INVENTION

There exists a need for enzymes such as proteases that have altered properties. As such, the present invention provides modified enzymes that have one or more amino acid residues replaced by cysteine residues. The cysteine residues are modified by replacing the thiol hydrogen with a substituent group providing a thiol side chain selected from the group consisting of:

a) —$SR^1R^2$, wherein $R^1$ is an alkyl and $R^2$ is a charged or polar moiety;

b) —$SR^3$, wherein $R^3$ is a substituted or unsubstituted phenyl;

c) —$SR^4$, wherein $R^4$ is substituted or unsubstituted cyclohexyl; and d) —$SR^5$, wherein $R^5$ is $C_{10}$–$C_{15}$ alkyl.

In preferred embodiments, the thiol side chain groups —$SR^3$ and —$SR^4$ above, further comprise an alkyl group, R, which is placed before either $R^3$ or $R^4$ to form —$SRR^3$ or —$SRR^4$. R is preferably a $C_{1-10}$ alkyl.

With regard to the thiol side chain group —$SR^1R^2$, $R^2$ can be positively or negatively charged. Preferably, $R^2$ is $SO_3^-$, $COO^-$ or $NH_3^+$. Further, $R^1$ is preferably a $C_{1-10}$ alkyl.

Preferably, the enzyme is a protease. More preferably, the enzyme is a Bacillus subtilisin. Also, preferably, the amino acids therein replaced by cysteines are selected from the group consisting of asparagine, leucine, methionine or serine. More preferably, the amino acid to be replaced is located in a subsite of the protease, preferably, the $S_1$, $S_1'$ or $S_2$ subsites. Most preferably, the amino acids to be replaced are N62, L217, M222, S156 and S166 where the numbered position corresponds to naturally-occurring subtilisin from *Bacillus amyloliquefaciens* or to equivalent amino acid residues in other subtilisins, such as *Bacillus lentus* subtilisin.

In a particularly preferred embodiment, the enzyme is a *Bacillus lentus* subtilisin. In the most preferred embodiments, the amino acid to be replaced by cysteine is N62 and the thiol side chain group is selected from the group:

—$S^1R^2$ wherein $R^1$ is $CH_2$ and $R^2$ is $CH_2SO_3^-$;

—$SRR^3$ wherein R is $CH_2$ and $R^3$ is $C_6H_5$;

—$SRR^4$ wherein R is $CH_2$ and $R^4$ is c-$C_6H_{11}$;

—$SR^5$ wherein $R^5$ is n-$C_{10}H_{21}$; or the amino acid to be replaced by cysteine is L217 and the thiol side chain group is —$SR^5$ wherein $R^5$ is n-$C_{10}H_{21}$.

The present invention further provides modified enzymes that have one or more amino acid residues replaced by cysteine residues. The cysteine residues are modified by replacing the thiol hydrogen with a substituent group providing a thiol side chain —$SR^6$ wherein $R^6$ is a $C_{1-6}$ alkyl and the amino acid residues to be replaced by cysteine are selected from the group consisting of asparagine, leucine, and serine. Preferably, the enzyme is a protease. More preferably, the enzyme is a Bacillus subtilisin. Most preferably, the amino acid is located in a subsite of the protease, preferably, the $S_1$, $S_1'$ or $S_2$ subsites. Most preferably, the amino acids to be replaced are N62, L217, M222, S156 and S166. Preferably, the enzyme is a *B. lentus* subtilisin, the amino acid to be replaced by a cysteine is N62 or L217 and the thiol side chain group is —$SR^6$ wherein $R^6$ is $CH_2C(CH_3)_3$ or $C_5H_{11}$.

The present invention provides a method of producing a modified enzyme, including providing an enzyme wherein one or more amino acids have been replaced with cysteine residues and replacing the thiol hydrogen of the cysteine residue with a subtituent group providing a thiol side chain selected from the group consisting of:

a) —$SR^1R^2$, wherein $R^1$ is an alkyl and $R^2$ is a charged or polar moiety;
b) —$SR^3$, wherein $R^3$ is a substituted or unsubstituted phenyl;
c) —$SR^4$, wherein $R^4$ is substituted or unsubstituted cyclohexyl; and
d) —$SR^5$, wherein $R^5$ is $C_{10}$–$C_{15}$ alkyl.

In preferred embodiments, the thiol side chain groups —$SR^3$ and —$SR^4$ above, further comprise an alkyl group, R, which is placed before either $R^3$ or $R^4$ to form —$SRR^3$ or —$SRR^4$. R is preferably a $C_{1-10}$ alkyl.

With regard to the thiol side chain group —$SR^1R^2$, $R^2$ can be positively or negatively charged. Preferably, $R^2$ is $SO_3^-$, $COO^-$ or $NH_3^+$. Further, $R^1$ is preferably a $C_{1-10}$ alkyl.

Preferably, the enzyme is a protease. More preferably, the enzyme is a Bacillus subtilisin. Also, preferably, the amino acids therein replaced by cysteines are selected from the group consisting of asparagine, leucine, methionine or serine. More preferably, the amino acid to be replaced is located in a subsite of the protease, preferably, the $S_1$, $S_1'$ or $S_2$ subsites. Most preferably, the amino acids to be replaced are N62, L217, M222, S156 and S166 where the numbered position corresponds to naturally-occurring subtilisin from *Bacillus amyloliquefaciens* or to equivalent amino acid residues in other subtilisins, such as *Bacillus lentus* subtilisin.

In a particularly preferred embodiment, the enzyme is a *Bacillus lentus* subtilisin. In the most preferred embodiments, the amino acid to be replaced by cysteine is N62 and the thiol side chain group is selected from the group:

—$S^1R^2$ wherein $R^1$ is $CH_2$ and $R^2$ is $CH_2SO_3$;
—$SRR^3$ wherein R is $CH_2$ and $R^3$ is $C_6H_5$;
—$SRR^4$ wherein R is $CH_2$ and $R^4$ is $c$-$C_6H_{11}$;
—$SR^5$ wherein $R^5$ is n-$C_{10}H_{21}$; or the amino acid to be replaced by cysteine is L217 and the thiol side chain group is —$SR^5$ wherein $R^5$ is n-$C_{10}H_{21}$.

The present invention further provides modified enzymes that have one or more amino acid residues replaced by cysteine residues. The cysteine residues are modified by replacing the thiol hydrogen with a substituent group providing a thiol side chain —$SR^6$ wherein $R^6$ is a $C_{1-6}$ alkyl and the amino acid residues to be replaced by cysteine are selected from the group consisting of asparagine, leucine, and serine. Preferably, the enzyme is a protease. More preferably, the enzyme is a Bacillus subtilisin. Most preferably, the amino acid is located in a subsite of the protease, preferably, the $S_1$, $S_1'$ or $S_2$ subsites. Most preferably, the amino acids to be replaced are N62, L217, M222, S156 and S166. Preferably, the enzyme is a *B. lentus* subtilisin, the amino acid to be replaced by a cysteine is N62 or L217 and the thiol side chain group is —$SR^6$ wherein $R^6$ is $CH_2C(CH_3)_3$ or $C_5H_{11}$.

There are further provided detergent additives that include modified enzymes.

There are provided feed additives that include modified enzymes.

There is provided methods of using the modified enzymes in a detergent formulation.

There is provided methods of using the modified enzymes in the treatment of fabric.

There is provided methods of using the modified enzymes in the preparation of a feed additive.

There are provided modified enzymes having increased activity.

There are provided modified enzymes having altered pH profiles.

There are provided modified enzymes having improved wash performance.

There are provided methods of using the modified enzymes in organic synthesis.

DETAILED DESCRIPTION OF THE INVENTION

Figure 1:
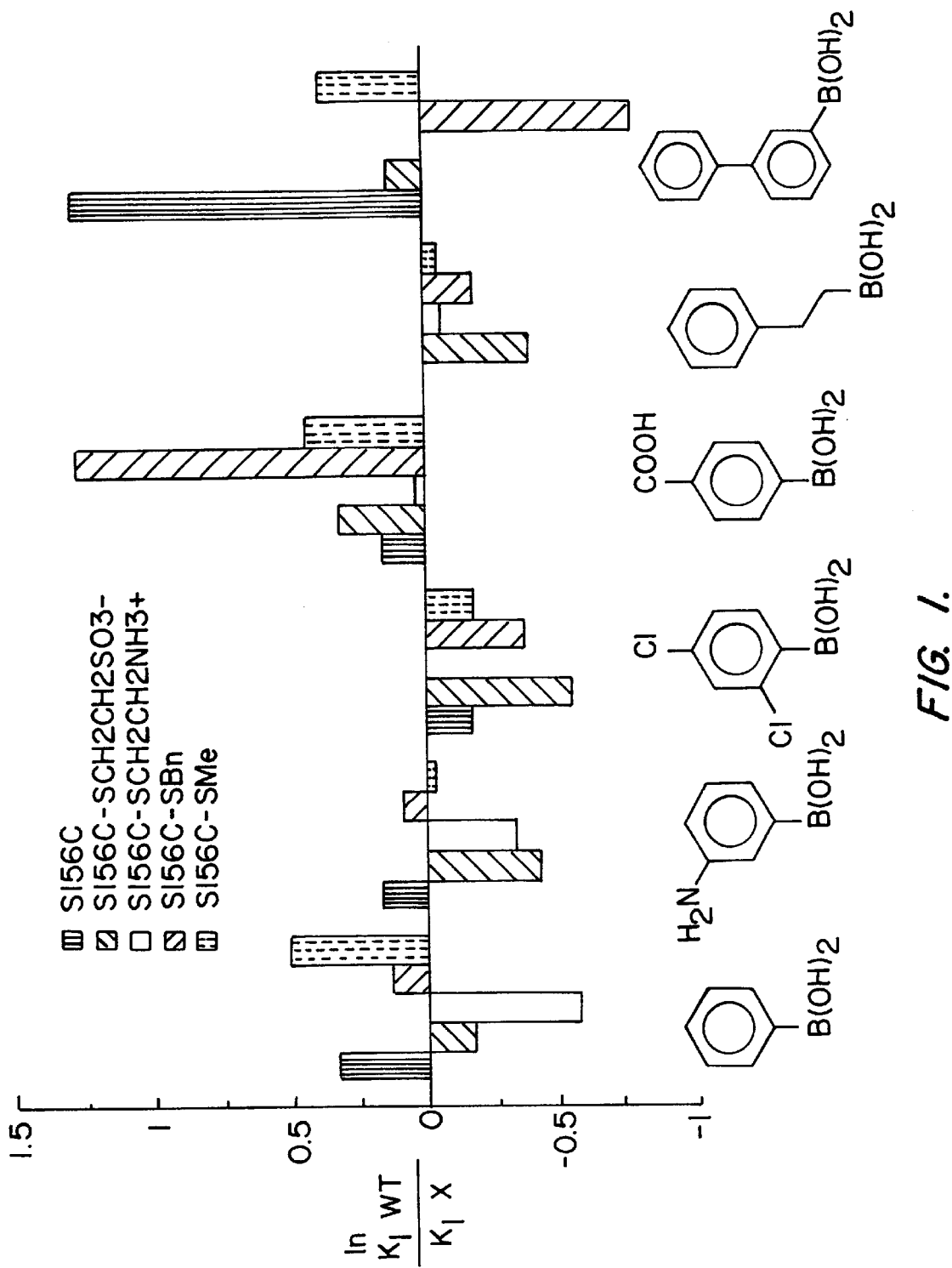
FIG. 1 is a bar graph of the results obtained after probing modified S156C mutants with boronic inhibitors at pH 8.6.

In one embodiment of the invention, a modified enzyme and a method of providing such are provided that has one or more amino acid residues of a subtilisin replaced by cysteine residues. The cysteine residues are then modified by replacing the thiol hydrogen with a substituent group providing a thiol side chain selected from the group consisting of:

a) —$SR^1R^2$, wherein $R^1$ is an alkyl and $R^2$ is a charged or polar moiety;
b) —$SR^3$, wherein $R^3$ is a substituted or unsubstituted phenyl;
c) —$SR^4$, wherein $R^4$ is substituted or unsubstituted cyclohexyl; and
d) —$SR^5$, wherein $R^5$ is $C_{10}$–$C_{15}$ alkyl.

In preferred embodiments, the thiol side chain groups —$SR^3$ and —$SR^4$ above, further comprise an alkyl group, R, which is placed before either $R^3$ or $R^4$ to form —$SRR^3$ or —$SRR^4$. R is preferably a $C_{1-10}$ alkyl.

With regard to the thiol side chain group —$SR^1R^2$, $R^2$ can be positively or negatively charged. Preferably, $R^2$ is $SO_3^-$, $COO^-$ or $NH_3^+$. Further, $R^1$ is preferably a $C_{1-10}$ alkyl.

Preferably, the enzyme is a protease. More preferably, the enzyme is a Bacillus subtilisin. Also, preferably, the amino acids therein replaced by cysteines are selected from the group consisting of asparagine, leucine, methionine or serine. More preferably, the amino acid to be replaced is located in a subsite of the protease, preferably, the $S_1$, $S_1'$ or $S_2$ subsites. Most preferably, the amino acids to be replaced are N62, L217, M222, S156 and S166 where the numbered position corresponds to naturally-occurring subtilisin from *Bacillus amyloliquefaciens* or to equivalent amino acid residues in other subtilisins, such as *Bacillus lentus* subtilisin.

In a particularly preferred embodiment, the enzyme is a *Bacillus lentus* subtilisin. In the most preferred embodiments, the amino acid to be replaced by cysteine is N62 and the thiol side chain group is selected from the group:

—$S^1R^2$ wherein $R^1$ is $CH_2$ and $R^2$ is $CH_2SO_3^-$;
—$SRR^3$ wherein R is $CH_2$ and $R^3$ is $C_6H_5$;
—$SRR^4$ wherein R is $CH_2$ and $R^4$ is $c$-$C_6H_{11}$;
—$SR^5$ wherein $R^5$ is n-$C_{10}H_{21}$; or the amino acid to be replaced by cysteine is L217 and the thiol side chain group is —$SR^5$ wherein $R^5$ is n-$C_{10}H_{21}$.

The present invention further provides modified enzymes that have one or more amino acid residues replaced by cysteine residues. The cysteine residues are modified by replacing the thiol hydrogen with a substituent group providing a thiol side chain —$SR^6$ wherein $R^6$ is a $C_{1-6}$ alkyl and the amino acid residues to be replaced by cysteine are selected from the group consisting of asparagine, leucine, and serine. Preferably, the enzyme is a protease. More preferably, the enzyme is a Bacillus subtilisin. Most preferably, the amino acid is located in a subsite of the protease, preferably, the $S_1$, $S_1'$ or $S_2$ subsites. Most preferably, the amino acids to be replaced are N62, L217, M222, S156 and S166. Preferably, the enzyme is a *B. lentus* subtilisin, the amino acid to be replaced by a cysteine is N62 or L217 and the thiol side chain group is —$SR^6$ wherein $R^6$ is $CH_2C(CH_3)_3$ or $C_5H_{11}$.

A "modified enzyme" is an enzyme that has been changed by replacing an amino acid residue such as asparagine, serine, methionine or leucine with a cysteine residue and then replacing the thiol hydrogen of the cysteine with a substituent group providing a thiol side chain, i.e., a group such as a $C_{1-6}$ alkyl or a $C_{10-15}$ alkyl or a group that includes a phenyl group, a cyclohexyl group or a charged or polar moiety. After modification, the properties of the enzyme, i.e., activity or substrate specificity, may be altered. Preferably, the activity of the enzyme is increased.

The term "enzyme" includes proteins that are capable of catalyzing chemical changes in other substances without being changed themselves. The enzymes can be wild-type enzymes or variant enzymes. Enzymes within the scope of the present invention include pullulanases, proteases, cellulases, amylases and isomerases, lipases, oxidases and reductases. The enzyme can be a wild-type or mutant protease. Wild-type proteases can be isolated from, for example, *Bacillus lentus* or *Bacillus amyloliquefaciens* (also referred to as BPN'). Mutant proteases can be made according to the teachings of, for example, PCT Publication Nos. WO 95/10615 and WO 91/06637.

Several types of moieties can be used to replace the thiol hydrogen of the cysteine residue. These include —$SR^1R^2$, —$SR^3$, —$SR^4$, —$SR^5$ or —$SR^6$. R and $R^1$ are independently defined as a substituted or unsubstituted $C_{1-10}$ alkyl. $R^2$ is a charged or polar group. $R^3$ is a substituted or unsubstituted phenyl group. $R^4$ is a substituted or unsubstituted cyclohexyl group. $R^5$ is a $C_{10-15}$ alkyl. $R^6$ is a $C_{1-6}$ alkyl. $R^1$, $R^5$ or $R^6$ can be substituted or unsubstituted and/or straight chain or branched chain. A charged group is one or more atoms that together form a charged molecule, i.e., $SO_3^-$, $COO^-$ or $NH_3^+$.

The terms "thiol side chain group", "substituent group providing a thiol side chain", "thiol containing group", and "thiol side chain" are terms which are can be used interchangeably and include groups that are used to replace the thiol hydrogen of the cysteine used to replace one of the amino acids in a subtilisin. Commonly, the thiol side chain group includes a sulfur through which the $R^x$ groups defined above are attached to the thiol sulfur of the cysteine.

The term "substituted" refers to a group of which a hydrogen of the group has been replaced with another atom or molecule. For example, a hydrogen can be substituted, for example, with a methyl group, a fluorine atom or a hydroxyl group. In the present invention, the alkyl groups, cyclohexyl group and phenyl group can be substituted, i.e., have substitutions of one or more hydrogen atoms with another atom or molecule.

The binding site of an enzyme consists of a series of subsites across the surface of the enzyme. The substrate residues that correspond to the subsites are labeled P and the subsites are labeled S. By convention, the subsites are labeled $S_1$, $S_2$, $S_3$, $S_4$, $S_1'$ and $S_2'$. A discussion of subsites can be found in Siezen et. al. (1991) *Protein Engineering* 4:719–737 and Fersht, A. E. (1985) *Enzyme Structure and Mechanism* 2 ed., Freeman (New York) pp. 29–30. The preferred subsites are $S_1$, $S_1'$ and $S_2'$.

The amino acid residues of the present invention can be replaced with cysteine residues using site-directed mutagenesis methods or other methods well known in the art. (See, for example, PCT Publication No. WO 95/10615.) A method of modifying the thiol hydrogen of the cysteine residue can be found in Example 4 below.

In one aspect of the invention, the modified protease has altered proteolytic activity as compared to the precursor protease, since increasing such activity (numerically larger) enables the use of the enzyme to more efficiently act on a target substrate. Also of interest are modified enzymes having altered activity, nucleophile specificity, substrate specificity, stereo selectivity, thermal stability, pH activity profile and surface binding properties as compared to the precursor.

Surprisingly, modified proteases of the present invention can have altered pKas and hence the pH profiles that are shifted from that of the precursor protease (see Example 7) without changing the surface charge of the protease molecule.

Modified enzymes of the invention can be formulated into known powdered and liquid detergents having pH between 6.5 and 12.0 at levels of about 0.01 to about 5% (preferably 0.1% to 0.5%) by weight. These detergent cleaning compositions or additives can also include other enzymes such as known proteases, amylases, cellulases, lipases or endoglycosidases, as well as builders and stabilizers.

Modified enzymes of the invention, especially subtilisins, are useful in formulating various detergent compositions. A number of known compounds are suitable surfactants useful in compositions comprising the modified enzymes of the invention. These include nonionic, anionic, cationic, anionic or zwitterionic detergents, as disclosed in U.S. Pat. No. 4,404,128 to Barry J. Anderson and U.S. Pat. No. 4,261,868 to Jiri Flora et al. A suitable detergent formulation is that described in Example 7 of U.S. Pat. No. 5,204,015. The art is familiar with the different formulations which can be used as cleaning compositions. In addition to typical cleaning compositions, it is readily understood that the modified enzymes of the present invention may be used for any purpose that native or wild-type enzymes are used. Thus, these modified enzymes can be used, for example, in bar or liquid soap applications, dishcare formulations, contact lens cleaning solutions or products, peptide synthesis, feed applications such as feed additives or preparation of feed additives, waste treatment, textile applications such as the treatment of fabrics, as fusion-cleavage enzymes in protein production, etc. The modified enzymes of the present invention may comprise improved wash performance in a detergent composition (as compared to the precursor). As used herein, improved wash performance in a detergent is defined as increasing cleaning of certain enzyme-sensitive stains such as grass or blood, as determined by light reflectance evaluation after a standard wash cycle.

The addition of the modified enzymes of the invention to conventional cleaning compositions does not create any special use limitation. In other words, any temperature and pH suitable for the detergent is also suitable for the present compositions as long as the pH is within the above range and the temperature is below the described modified enzyme's denaturing temperature. In addition, modified enzymes of the invention can be used in a cleaning composition without detergents, again either alone or in combination with builders and stabilizers.

In another aspect of the invention, the modified enzyme is used in the preparation of an animal feed, for example, a cereal-based feed. The cereal can be at least one of wheat, barley, maize, sorghum, rye, oats, triticale and rice. Although the cereal component of a cereal-based feed constitutes a source of protein, it is usually necessary to include sources of supplementary protein in the feed such as those derived from fish-meal, meat-meal or vegetables. Sources of vegetable proteins include at least one of full fat soybeans, rapeseeds, canola, soybean-meal, rapeseed-meal and canola-meal.

The inclusion of a modified enzyme of the present invention in an animal feed can enable the crude protein value and/or digestibility and/or amino acid content and/or digestibility coefficients of the feed to be increased, which permits a reduction in the amounts of alternative protein sources and/or amino acids supplements which had previously been necessary ingredients of animal feeds.

The feed provided by the present invention may also include other enzyme supplements such as one or more of β-glucanase, glucoamylase, mannanase, α-galactosidase, phytase, lipase, α-arabinofuranosidase, xylanase, α-amylase, esterase, oxidase, oxido-reductase and pectinase. It is particularly preferred to include a xylanase as a further enzyme supplement such as a subtilisin derived from the genus Bacillus. Such xylanase are for example described in detail in PCT patent publication WO 97/20920.

One aspect of the invention is a composition for the treatment of a textile that includes MP. The composition can be used to treat for example silk or wool as described in publications such as RD 216,034; EP 134,267; U.S. Pat. No. 4,533,359; and EP 344,259.

The modified enzymes of the present invention can be used in organic synthesis to, for example, catalyze a desired reaction and/or favor a certain stereoselectivity. See, for example, Noritomi et al. *Biotech. Bioeng.* 51:95–99 (1996); Dabulis et al. *Biotech. Bioeng.* 41:566–571 (1993); Fitzpatrick et al. *J. Am. Chem. Soc.* 113:3166–3171 (1991).

The following is presented by way of example and is not to be construed as a limitation to the scope of the claims.
Experimental

EXAMPLE 1
Producing the Cys-Mutants

The gene for subtilisin from *B. lentus* (SBL) was cloned into the bacteriophage M13mp19 vector for mutagenesis. (U.S. Pat. No. 5,185,258.) Oligonucleotide-directed mutagenesis was performed as described in Zoller et al. (1983) *Methods Enzymol.* 100:468–500. The mutated sequences were cloned, excised and reintroduced into the expression plasmid GG274 in the *B. subtilis* host. PEG (50%) was added as a stabilizer. The crude protein concentrate obtained was purified by first passing through a Sephadex™ G-25 desalting matrix with a pH 5.2 buffer (20 mM sodium acetate, 5 mM $CaCl_2$) to remove small molecular weight contaminants. Pooled fractions for the desalting column were then applied to a strong cation exchange column (SP Sepharose™ FF) in the sodium acetate buffer (above), and SBL was eluted with a one step gradient of 0–200 mM NaCl acetate buffer, pH 5.2. Salt-free enzyme powder was obtained following dialysis of the eluent against Millipore purified water, and subsequent lyophilization. The purity of the mutant and wild-type enzymes, which had been denatured by incubation with 0.1 M HCl at 0° C. for 30 minutes, was ascertained by SDS-PAGE on homogeneous gels using the Phast™ System from Pharmacia (Uppsala, Sweden). The concentration of SBL was determined using the Bio-Rad (Hercules, Calif.) dye reagent kit which is based on the method of Bradford (1976) *Analytical Biochemistry* 72:248–254. Specific activity of the enzymes was determined in pH 8.6 buffer using the method described below.

EXAMPLE 2
Preparation of Certain Moieties
3-methylbutyl Methanethiosulfonate The reaction mixture of 1-bromo-3-methylbutane (1.7520 g, 0.0116 mol) and sodium methanethiosulfonate (1.554 g, 0.0116 mol) in dry DMF (5 mL) was heated at 50° C. for 2 hr. At room temperature, water (15 mL) was added and the mixture was extracted with ether (3×30 mL). The combined extracts were washed with brine, dried, concentrated. The residue was subjected to flash column chromatography on silica gel with EtOAc-hexanes (1:4). The product was obtained as a colorless liquid (1.4777 g, 70%). IR (film): 3030 (w), 3011 (w), 2958 (st), 2932 (st), 2873 (st), 1468 (m), 1410 (w), 1388 (w), 1367 (w), 1319 (st), 1136 (st), 955 (st), 748 $cm^{-1}$ (st); $^1$H NMR (200 MHz, $CDCl_3$): δ 3.33 (s, 3H, $CH_3SO_2S$); 3.19 (t, J=7.1 Hz, 2H, $SCH_2CH_2$), 1.70–1.58 (m, 3H, $SCH_2CH_2CHMe_2$), 0.95 (d, J=5.3 Hz, 6H, $CHMe_2$); $^{13}$C NMR (50 MHz, $CDCl_3$): δ 50.60, 38.19, 34.59, 27.40, 22.06.

Neopentyl Methanethiosulfonate

The reaction mixture of neopentyl iodide (3.054 g, 0.0154 mol), sodium methanethiosulfonate (2.272 g, 0.0170 mol) and dry DMF (4 mL) was heated at 90° C. for 90 hr. The reaction flask was wrapped with aluminum foil to avoid direct sunlight to the reaction mixture, since the iodide was sensitive to sunlight. At the end of the heating, the reaction mixture was red-brown in color. At room temperature, water (15 mL) was added and the mixture was extracted with ether (3×30 mL). The combined ether extracts were washed twice with brine, dried, concentrated and the residue was subjected to column chromatography on silica gel with EtOAc-hexanes (1:2) to afford a colorless oil which slowly solidified (1.2395 g, 44%). The product was recrystallized from 95% EtOH. mp: 28.5–29.0° C.; IR ($CH_2Cl_2$ cast): 3021 (m), 2956 (m), 2868 (m), 1467 (m), 1433 (m), 1321 (st), 1310 (st), 1125 (st), 951 (m), 757 (m) and 724 $cm^{-1}$ (m); $^1$H NMR (200 MHz, $CDCl_3$): δ 3.32 (s, 3H, $CH_3SO_2S$), 3.13 (s, 2H, $SCH_2C$), 1.05 (s, 9H, $CMe_3$); $^{13}$C NMR (50 MHz, $CDCl_3$): δ 50.23, 50.09, 32.14, 28.79, MS (EI): 182 ($M^+$), 57 (base peak, $CMe_3^+$).

Hexyl Methanethiosulfonate

The reaction mixture of 1-bromohexane (1.046 g, 0.00635 mol), sodium methanethiosulfonate (0.850 g, 0.00635 mol) and dry DMF (6 mL) was heated at 60° C. for 2 hr. At room temperature, water (15 mL) was added and the resulting mixture was extracted with ether (3×30 mL). The extracts were washed with brine, dried, concentrated and the residue was subjected to flash column chromatography on silica gel with EtOAc-hexanes (1:4) to afford a colorless liquid (2.057 g, 82%). IR ($CDCl_3$ cast): 3030 (w), 3010 (w), 2955 (st), 2930 (st), 2860 (st), 1460 (m), 1320 (st), 1133 (st), 955 (st), 747 $cm^{-1}$ (st); $^1$H NMR (200 MHz, $CDCl_3$): δ 3.33 (s, 3H, $CH_3SO_2S$), 3.18 (t, J=7.4 Hz, 2H, $SCH_2CH_2$), 1.77 (pseudo p, J=7.2 Hz, 2H, $SCH_2CH_2$), 1.50–1.20 (m, 6H, $CH_2CH_2CH_2CH_3$), 0.90 (m, 3H, $CH_2CH_3$); $^{13}$C NMR (50 MHz, $CDCl_3$): δ 50.64, 36.50, 31.13, 29.46, 28.26, 22.44, 13.96.

Cyclohexylmethyl Methanethiosulfonate

The reaction mixture of bromomethylcyclohexane (1.560 g, 0.00881 mol), sodium methanethiosulfonate (1.180 g, 0.00881 mol) and dry DMF (6 mL) was heated at 50° C. for 24 hr. At room temperature, water (15 mL) was added and the mixture was extracted with ether (3×30 mL). The extracts were washed with brine, dried, concentrated and the residue was subjected to flash column chromatography on silica gel with EtOAc-hexanes (1:4) to afford a colorless oil (1.5033 g, 82%). IR (CDCl$_3$ cast): 3030 (w), 3012 (w), 2926 (st), 2853 (st), 1446 (m), 1410 (m), 1320 (st), 1134 (st), 955 (st), 746 cm$^{-1}$ (st); $^1$H NMR (200 MHz, CDCl$_3$): δ 3.32 (s, 3H, CH$_3$SO$_2$S), 3.07 (d, J=6.9 Hz, 2H, SCH$_2$CH), 1.95–1.55 (m, 6H), 1.40–0.90 (m, 5H); $^{13}$C NMR (50 MHz, CDCl$_3$): δ 50.42, 43.30, 37.83, 32.43, 26.02, 25.82.

Decyl Methanethiosulfonate

The mixture of 1-bromodecane (2.095 g, 0.00947 mol), sodium methanethiosulfonate and dry DMF (6 mL) was heated at 60° C. for 2 hr. At room temperature, water (15 mL) was added and the mixture was extracted with ether (3×30 mL). The ether extracts were washed with brine, dried, concentrated and the residue was subjected to flash column chromatography on silica gel with EtOAc-hexanes (1:4) to afford a white solid (2.063 g, 94%). It was recrystallized from 95% EtOH. mp: 28.0–29.5° C. IR (CDCl$_3$ cast): 2954 (m), 2921 (st), 2852 (st), 1469 (m), 1305 (st), 1128 (st), 965 (m), 758 (m) and 720 cm$^{-1}$ (m); $^1$H NMR (200 MHz, CDCl$_3$): δ 3.32 (s, 3H, CH$_3$SO$_2$S), 3.17 (t, J=7.4 Hz, 2H, SCH$_2$CH$_2$), 1.77 (m, 2H, SCH$_2$CH$_2$), 1.50–1.20 (m, 14H, —(CH$_2$)$_7$—), 0.88 (m, 3H, CH$_2$CH$_3$); $^{13}$C NMR (50 MHz, CDCl$_3$): δ 50.64, 36.49, 31.84, 29.45 (two carbons), 29.37, 29.23, 28.94, 28.57, 22.64, 14.08.

Sodium Methanethiosulfonate

Mesyl chloride (46.6 mL, 0.602 mol) was added dropwise to a solution of Na$_2$S.9H$_2$O (142.2 g, 0.592 mol) in water (150 mL) at 80° C. After the addition, the reaction mixture was heated under reflux and it turned from pale yellow to yellow in 15 hr. During this time, some yellow precipitates were also formed. The reaction mixture was cooled to room temperature and the water was evaporated. After the solid residue was ground with a mortar and pestle and the powder was dried further at 50° C. and 1 torr. Absolute ethanol (700 mL) was used to triturate the powder in 4 portions and the ethanol filtrate was concentrated and cooled with an ice bath to obtain a precipitate which was collected by vacuum filtration. The filtrate was concentrated further to obtain a second crop of precipitates. After repeated concentration and filtration (4×), the final volume of the filtrate was approximately 10 mL. The combined precipitates were redissolved in absolute ethanol at room temperature and filtered to remove trace amounts of sodium chloride and sodium sulfide. The filtrate was concentrated and cooled and the solids collected by vacuum filtration. Again, the concentration, cooling and filtration process was repeated 3 times to give white, flaky crystals, which were dried further at 1 torr overnight. (24.51 g, 31%) IR (KBr): 3004, 2916, 1420, 1326, 1203, 1095, 980, 772 cm$^{-1}$. $^1$H NMR (200 MHz, D$_2$O): δ 3.23 (s). $^{13}$C NMR (50 MHz, D$_2$O, with DMSO-d$_6$ as an internal standard): δ 39.72 ppm.

Benzyl Methanethiosulfonate

Benzyl bromide (9.07 g, 0.053 mol) was slowly added to a suspension of sodium methanethiosulfonate (7.10 g, 0.0530 mol) in absolute EtOH (100 mL) and the reaction mixture was heated at reflux overnight. The reaction mixture was cooled with an ice bath and the solid (sodium bromide and sodium methanethiosulfonate) was filtered off. The filtrate was concentrated to give a crude product which was mainly the desired product. Pure product was obtained by flash chromatography on silica gel with EtOAc-hexanes (1:6) (7.92 g, 74%). The product was further purified by recrystallization from absolute ethanol. mp 39.5–40.2° C. (lit. 40–42.5° C.) IR (KBr): 3089, 3068, 3017, 3000, 2981, 2936, 2918, 1602, 1582, 1496, 1305, 1131, 960, 771, 741, 702 cm$^{-1}$. $^1$H NMR (200 MHz, CDCl$_3$): δ 7.38 (m, 5H, phenyl), 4.38 (s, 2H, SCH$_2$), 2.91 (s, 3H, CH$_3$SO$_2$). $^{13}$C NMR (50 MHz, CDCl$_3$): δ 135.12, 129.14, 129.03, 128.26, 51.09, 40.79.

The reagents CH$_3$SO$_2$—SCH$_2$CH$_2$SO$_3^-$Na$^+$ and CH$_3$SO$_2$—SCH$_2$CH$_2$NH$_3^+$Br$^-$ were purchased from Toronto Research Chemicals (Toronto, Ontario).

EXAMPLE 3

Modification of the Cys-Mutants

The following is exemplary for the method used to modify the Cys-mutants, i.e., N62C.

Modification of M222C

To a solution of the Cys-mutant, M222C, *B. lentus* (25.1 mg, 0.94 μmol) in buffer (250 ml; 70 mM CHES, 5 mM MES, 2 mM CaCl$_2$, pH 9.5) in a polypropylene test tube which had been precoated with a water solution of polyethylene glycol 10,000 (0.1% w/v), was added a solution of methyl methanethiosulfonate described in Example 2 in 95% EtOH (100 μl, 92.4 μmol). The solution was vortexed and allowed to slowly rotate on an end-over-end rotator at room temperature (22° C.). One blank containing ethanol instead of the reagent-solution was run in parallel. The modification was followed by activity measurements on 10 μl withdrawn samples and was determined according to the method described above. The reaction was terminated after 2.5 hours when addition of another aliquot of reagent to the reaction did not change the activity of the protease. The solution (2.5 ml) was purified on a disposable desalting column (Pharmacia Biotech PD-10™, Sephadex™ G-25M). The column was equilibrated with buffer (25 ml; 5 mM MES, 2 mM CaCl$_2$, pH 6.5) and the sample was loaded on top. The initial 2.5 ml collected was discarded. Protein was eluted with MES-buffer (3.5 ml) and collected in three fractions. All fractions appeared as one single band when checked on gel (SDS-PAGE, Pharmacia Phast-System™) and could not be differentiated from the Cys-mutant or the wild-type which both were run as references. The three fractions were mixed and dialyzed against deionized water (3×1 l) at 0° C., followed by lyophilization overnight which gave the modified mutant (14.3 mg). The specific activity was 64.3 U/mg as compared with the Cys mutant (47.1 U/mg).

Measuring the Activity of the Modified Proteases

Activity, including the kinetic parameters k$_{cat}$, K$_M$, and k$_{cat}$/K$_M$ were measured for hydrolysis of the synthetic peptide substrate succinyl-L-Ala-L-Ala-L-Pro-L-Phe-p-nitroanilide using the method described in Bonneau, P. et al. (1991) *J. Am. Chem. Soc.*, 113(3):1030. Briefly, a small aliquot of subtilisin variant stock solution was added to a 1 cm cuvette containing substrate dissolved in 0.1 M sodium phosphate buffer, pH 7.5, containing 0.5 M NaCl and 1% DMSO, and thermostated at 25° C. or similarly at pH 8.6, 0.1 M tris buffer containing 0.05% Tween™80 and 1% DMSO. The reaction progress was followed spectrophotometrically by monitoring the absorbance of the reaction product p-nitroaniline at 410 nm using a Perkin Elmer λ2 spectrophotometer (Δε$_{410}$ 8800 M$^{-1}$ cm$^{-1}$). Kinetic parameters were obtained by measuring initial rates at substrate concentrations of 0.25 mM–4.0 mM (eight concentrations) and fitting this data to the Michaelis-Menten equation.

Table 1 shows the abbreviations for certain of the thiosulfonates. Table 2 shows the kinetic parameters of the modified *B. lentus* subtilisins (SBL) and the precursor subtilisin (SBL-WT) at pH 7.5. The modified enzymes were prepared as described above after site-directed mutagenesis to replace the amino acid of interest with a cysteine. The kinetic parameters were determined at pH 7.5 as described above. The precursor protease was a *Bacillus lentus* subtilisin (SBL-WT).

TABLE 1

| Abbreviation | Structure |
| --- | --- |
| -SBn | $-SCH_2C_6H_5$ |
| -Siso-butyl | $-SCH_2CH(CH_3)_2$ |
| -Sneo-pentyl | $-SCH_2C(CH_3)_3$ |
| $-SCH_2$cyclohexyl | $-SCH_2$-c-$C_6H_{11}$ |
| -Sdecyl | $-S$-n-$C_{10}H_{21}$ |

TABLE 2

| Enzyme | $K_M$ (mM) | $k_{cat}$ (s$^{-1}$) | $k_{cat}/K_M$ |
| --- | --- | --- | --- |
| SBL-WT | 0.55 | 48 | 87 |
| N62C | 1.49 | 61 | 41 |
| N62C-$SCH_2CH_2NH_3^+$ | 1.2 | 63 | 52 |
| N62C-$SCH_2CH_2SO_3^-$ | 0.83 | 66 | 86 |
| N62C-Siso-butyl | 0.84 | 76 | 90 |
| N62C-SBn | 0.37 | 70 | 189 |
| N62C-Sneo-pentyl | 0.78 | 96 | 123 |
| N62C-S-hexyl | 0.54 | 136 | 252 |
| N62C-$SCH_2$cyclohexyl | 0.48 | 135 | 281 |
| N62C-Sdecyl | 0.35 | 69 | 197 |
| L217C | 0.9 | 16.1 | 18 |
| L217C-$SCH_2CH_2NH_3^+$ | 0.71 | 12.4 | 17 |
| L217C-$SCH_2CH_2SO_3^-$ | 0.77 | 20.6 | 27 |
| L217C-Siso-butyl | 0.53 | 37 | 70 |
| L217C-SBn | 0.65 | 31.6 | 49 |
| L217C-Sneo-pentyl | 0.47 | 40 | 85 |
| L217C-Shexyl | 0.45 | 61 | 136 |
| L217C-$SCH_2$cyclohexyl | 0.51 | 29.8 | 58 |
| L217C-Sdecyl | 0.55 | 77 | 140 |
| M222C | 0.77 | 17.3 | 22 |
| M222C-$SCH_2CH_2NH_3^+$ | 0.61 | 1.06 | 1.7 |
| M222C-$SCH_2CH_2SO_3^-$ | 0.55 | 1.64 | 3 |
| M22C-SBn | 0.67 | 6.9 | 10 |
| S156C | 0.65 | 43 | 66 |
| S156C-$SCH_2CH_2NH_3^+$ | 0.86 | 39 | 45 |
| S156C-$SCH_2CH_2SO_3^-$ | 0.78 | 31.6 | 40 |
| S156C-Siso-butyl | 0.60 | 24.2 | 40 |
| S156C-SBn | 0.54 | 21.8 | 40 |
| S166C | 0.51 | 14.2 | 28 |
| S166C-$SCH_2CH_2NH_3^+$ | 0.60 | 16.3 | 27 |
| S166C-$SCH_2CH_2SO_3^-$ | 0.70 | 3.8 | 5.4 |
| S166C-Siso-butyl | 0.91 | 29 | 32 |
| S166C-SBn | 0.74 | 6.9 | 9 |

EXAMPLE 4

Altering the Specificity of the *B. lentus* Subtilisin

Changes in substrate specificity, particularly the $S_1$ subsite specificity, can be shown by using various boronic acids as competitive inhibitors. Four of the modified S156C mutants and three of the modified S166C mutants described above were evaluated using boronic acid inhibitors. The modified mutants were S156C—SMe, S156C—SBn, S156C—$SCH_2CH_2SO_3^-$, S156C—$SCH_2CH_2NH_3+$, S166C—$SCH_2CH_2SO_3^-$, S166C—$SCH_2CH_2NH_3^+$, and S166C—SBn.

Figure 2:
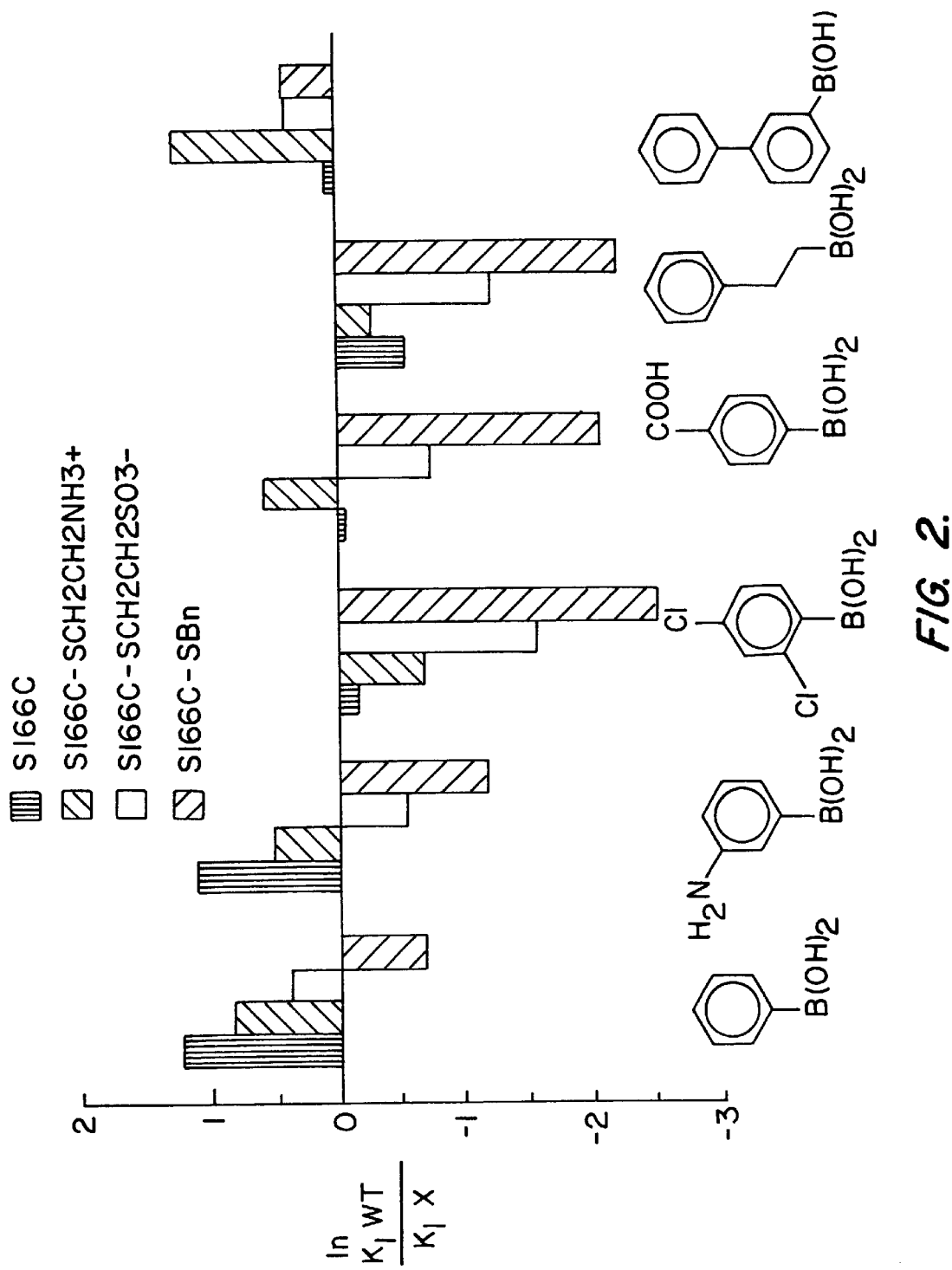
FIG. 2 is a bar graph of the results obtained after probing modified S166C mutants with boronic inhibitors at pH 8.6.

The boronic acids were prepared, and their inhibition constants measured at pH 8.6 (Waley (1982) *Biochem. J. b 205:631–33*), as previously described in Seufer-Wasserthal et al. (1994) *Bioorpanic and Medicinal Chemistry 2:35–48*). The results are shown in FIGS. 1 and 2.

EXAMPLE 5

Wash Performance Test

The wash performance of several of the modified enzymes described in the previous examples was evaluated by measuring the removal of stain from EMPA 116 (blood/milk/carbon black on cotton) cloth swatches (Testfabrics, Inc., Middlesex, N.J. 07030) which had been pre-bleached in the following manner: in a 4-liter glass beaker, 1.9 grams perborate tetrahydrate, 1.4 grams perborate monohydrate and 1 gram TAED (tetraacetylethylenediamine) were dissolved in 3 liters of deionized water at 60° C. for 1 minute with stirring. 36 EMPA 116 swatches were added and stirred for 3 minutes. The swatches were immediately rinsed with cold deionized water for 10 minutes. Swatches were laid flat on absorbent paper towels to dry overnight.

Five pre-bleached EMPA 116 swatches were placed in each pot of a Model 7243S Tergotometer (United States Testing Co., Inc., Hoboken, N.J.) containing 1000 ml of water, 3 gpg hardness ($Ca^{++}$:$Mg^{++}$::3:1::w:w), 0.67 g of detergent with bleach and enzyme as appropriate. The detergent base was WFK1 detergent from wfk-Testgewebe GmbH, Adlerstrasse 42, Postfach 13 07 62, D-47759 Krefeld, Germany.

| Detergent Base Component | % of Final Formulation |
| --- | --- |
| Zeolite A | 25% |
| Sodium sulfate | 25% |
| Soda ash | 10% |
| Linear alkylbenzenesulfonate | 8.8% |
| Alcohol ethoxylate (7-8 EO) | 4.5% |
| Sodium soap | 3% |
| Sodium silicate ($SiO_2$:$Na_2O$::3.3:1) | 3% |

To this base detergent, the following additions were made:

| Bleach Component | % of Final Formulation |
| --- | --- |
| Sodium perborate monohydrate | 7% |
| Sodium perborate tetrahydrate | 9.2% |
| TAED | 4.5% |

Sodium perborate monohydrate and sodium perborate tetrahydrate were obtained from Degussa Corporation, Ridgefield Park, N.J. 07660. TAED (tetraacetylethylenediamine) was obtained from Warwick International, Limited, Mostyn, Holywell, Clwyd CH8 9HE, England.

The pre-bleached EMPA 116 swatches were washed in detergent with 0.1 ppm enzyme for 20 minutes at 20° C. and were subsequently rinsed twice for 5 minutes in 1000 ml water. Swatches were dried and pressed, and the reflectance from the swatches measured using the L value on the lab scale of a Minolta Chroma Meter, Model CR-200 (Minolta Corporation, Ramsey, N.J. 07446). Performance is reported as percent stain removal and percent stain removal relative to native *B. lentus* protease. Percent stain removal was calculated using the equation:

$$\frac{(L \text{ value washed swatches}) - (L \text{ value unwashed swatches}) \times 100}{(L \text{ value unstained } EMPA \text{ 221 swatches}) - (L \text{ value unwashed swatches})}$$

TABLE 3

| Enzyme | Percent Stain Removal | Percent Relative Stain Removal |
| --- | --- | --- |
| SBL-WT | 8.1 | 100 |
| N62C-SCH$_2$CH$_2$SO$_3^-$ | 13.4 | 165 |
| S166C-SCH$_2$CH$_2$SO$_3^-$ | 12.8 | 158 |
| L217C-SCH$_2$CH$_2$SO$_3^-$ | 13.2 | 163 |

EXAMPLE 7
Altering the pH Profile of a Precursor Subtilisin

Figure 3:
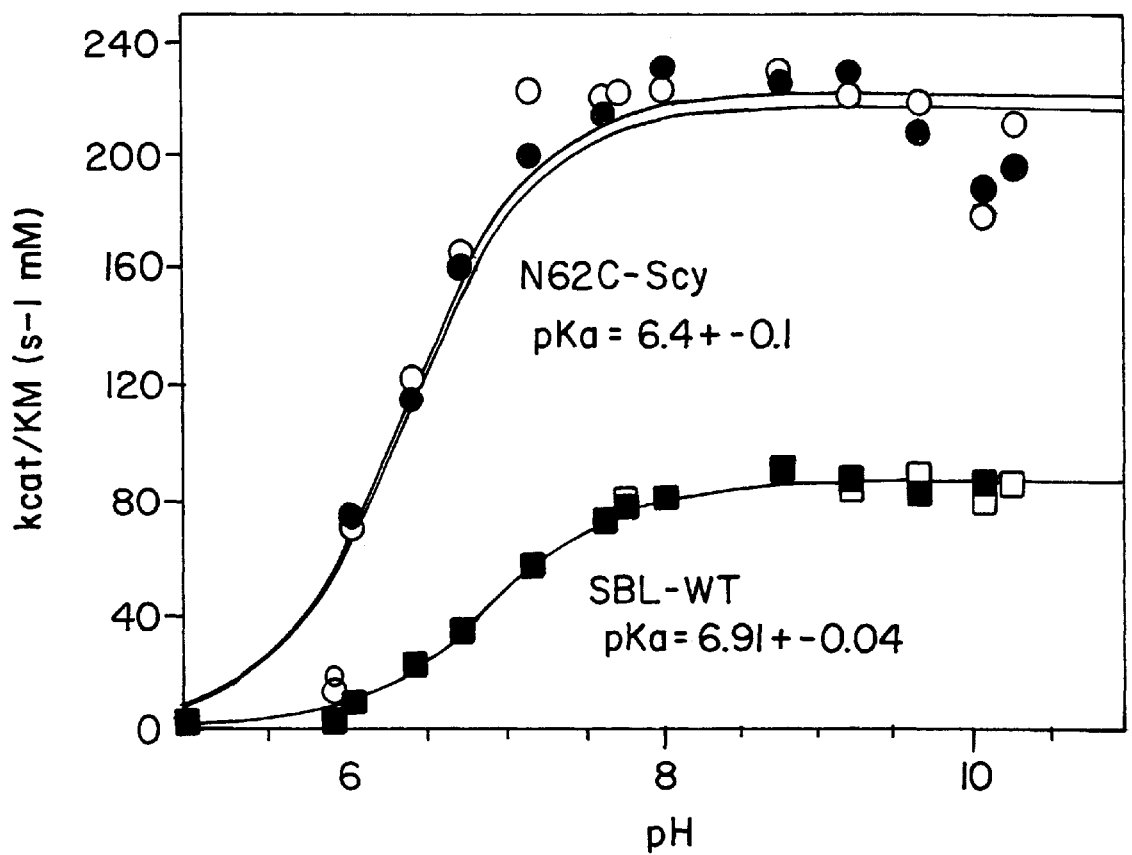
FIG. 3 is a graph of the pH profiles of wild type Bacillus lentus subtilisin (SBL-WT, squares) and a modified N62C mutant (N62C-Scy; circles). Points were done in duplicate.

To examine the effects of chemical modification on the pH profile of SBL, seven modified N62C mutants were made as described above. 0.02M ethylene diamine buffers of ionic strength 0.05M (adjusted with KCl) were employed with $1.25 \times 10^{-4}$ M succinyl-AAPF-pNA substrate and $K_{cat}/K_M$ measurements were performed as described above. $K_{cat}/K_M$ reflects the pKa of His64, part of the catalytic triad for SBL, in the free enzyme and is unaffected by nonproductive binding modes. Fersht, A. E. (1985) *Enzyme Structure and Mechanism* 2 ed., Freeman (New York). pKa was calculated using Graphit (McGeary & Associates, Middletown Conn.). The shift in pKa reflects a shift in the pH profile of SBL. Representative pH profiles for SBL N62C-Scylcohexyl (N62C-Scy) and SBL-WT are shown in FIG. 3 ([E]=$1 \times 10^{-7}$ to $5 \times 10^{-8}$M at 25° C.). Points were done in duplicate.

Table 4 shows the pKa of His64, change in pKa from the *B. lentus* wild type (WT) and the $k_{cat}/K_M$ for seven modified N62C SBL mutants.

TABLE 4

| SBL Enzyme | pKa of His64 | ΔpKa | K$_{cat}$/K$_M$ (s$^{-1}$mM$^{-1}$) |
| --- | --- | --- | --- |
| WT | 6.91 | — | 87 |
| N62C | 6.7 | 0.21 | 49 |
| N62C-SMe | 6.7 | 0.21 | 66 |
| N62C-SCH$_2$CH$_2$NH$_3^+$ | 6.62. | 0.29 | 52 |
| N62C-SCH$_2$CH$_2$SO$_3^-$ | 7 | 0.09 | 86 |
| N62C-Scyclohexyl | 6.4 | 0.51 | 281 |
| N62C-SBn | 6.71 | 0.20 | 189 |
| N62C-Sdecyl | 6.19 | 0.72 | 197 |

As shown in Table 4, a very dramatic 0.5 unit decrease in the pKa of His64 is observed for the N62C-Scyclohexyl modified SBL as compared to the wild type. As such, it is possible to engineer altered pH profiles without altering surface charge.

While the invention has been described in connection with specific embodiments thereof, it will be understood that it is capable of further modifications and this application is intended to cover any variations or adaptations of the invention following, in general, the principles of the invention and including such departures from the present disclosure as come within known or customary practice within the art to which the invention pertains and as can be applied to the essential features hereinbefore set forth, and as follows in the scope of the appended claims.

All publications and patents or applications referred to in the above specification are hereby incorporated by reference.

What is claimed is:

1. A modified subtilisin wherein one or more amino acid residues selected from the group consisting of amino acid residue 62, amino acid residue 217 amino acid residue 222, amino acid residue 156 and amino acid residue 166 are replaced by cysteine residues, wherein the cysteine residues are modified by replacing the thiol hydrogen with a substituent group providing a thiol side chain selected from the group consisting of:
   a) —SR$^1$R$^2$, wherein R$^1$ is an alkyl and R$^2$ is a charged or polar moiety;
   b) —SR$^3$, wherein R$^3$ is a substituted or unsubstituted phenyl;
   c) —SR$^4$, wherein R$^4$ is a substituted or unsubstituted cyclohexyl; and
   d) —SR$^5$, wherein R$^5$ is C$_{10}$–C$_{15}$ alkyl.

2. The modified enzyme of claim 1, wherein the cysteine residues are modified by replacing the thiol hydrogen with —SR$^1$R$^2$, wherein R$^1$ is an alkyl and R$^2$ is a charged or polar moiety.

3. The modified subtilisin of claim 2, wherein R$^1$ is C$_{1-10}$ alkyl.

4. The modified subtilisin of claim 2, wherein R$^2$ is positively charged.

5. The modified subtilisin of claim 4, wherein R$^2$ is NH$_3^+$.

6. The modified subtilisin of claim 2, wherein R$^2$ is negatively charged.

7. The modified subtilisin of claim 6, wherein R$^2$ is SO$_3$.

8. The modified subtilisin of claim 1, wherein said subtilisin is a *Bacillus lentus* subtilisin.

9. The modified subtilisin of claim 1, wherein the amino acid replaced with a cysteine is an amino acid selected from the group consisting of asparagine, leucine, methionine and serine.

10. The modified subtilisin of claim 9, wherein the modified amino acid is N62.

11. The modified subtilisin of claim 9, wherein the modified amino acid is M222.

12. The modified subtilisin of claim 9, wherein the modified amino acid is L217.

13. A method of producing a modified enzyme comprising:
   (a) providing a modified subtilisin wherein one or more amino acids selected from the group consisting of amino acid residue 62, amino acid residue 217, amino acid residue 222, amino acid residue 156, and amino acid residue 166 have been replaced with cysteine residues; and
   (b) replacing the thiol hydrogen of the cysteine with a substituent group providing a thiol side chain selected from the group consisting of:
      i) —SR$^1$R$^2$, wherein R$^1$ is an alkyl and R$^2$ is a charged or polar moiety;
      ii) —SR$^3$, wherein R$^3$ is a substituted or unsubstituted phenyl;
      iii) —SR$^4$, wherein R$^4$ is a substituted or unsubstituted cyclohexyl; and
      iv) —SR$^5$, wherein R$^5$ is C$_{10}$–C$_{15}$ alkyl.

14. The method of claim 13, wherein the thiol hydrogen is replaced with —SR$^1$R$^2$, wherein R$^1$ is an alkyl and R$^2$ is a charged or polar moiety.

15. The method of claim 14, wherein R$^1$ is C$_{1-10}$ alkyl.

16. The method of claim 14, wherein R$^2$ is positively charged.

17. The method of claim 16, wherein R$^2$ is NH$_3^+$.

18. The method of claim 14, wherein R$^2$ is negatively charged.

19. The method of claim 18, wherein R$^2$ is SO$_3$.

20. The method of claim 13, wherein the enzyme is a protease.

21. The method of claim 20, wherein the protease is a *Bacillus lentus* subtilisin.

22. The method of claim 13, wherein the amino acid replaced with a cysteine is an amino acid selected from the group consisting of asparagine, leucine, methionine and serine.

23. The method of claim 21, wherein the amino acid replaced with a cysteine is N62.

24. The method of claim 21, wherein the amino acid replaced with a cysteine is L217.

25. The method of claim 21, wherein the amino acid replaced with a cysteine is M222.

26. A detergent additive comprising the modified enzyme of claim 1, or 2.

27. A feed additive comprising the modified enzyme of claim 1, or 2.

28. A composition for the treatment of a textile comprising the modified enzyme of claim 1, or 2.

29. The modified enzyme of claim 1, wherein the enzyme is a *Bacillus lentus* subtilisin, the amino acid is N62, and the thiol side chain is —$SR^1R^2$, wherein $R^1$ is $CH_2CH_2$ and $R^2$ is $SO_3^-$.

30. The method of claim 13, wherein the amino acid replaced with a cysteine is an amino acid selected from the group consisting of asparagine, leucine, methionine, and serine.

31. The method of claim 13, wherein the amino acid replaced with a cysteine is in a subsite of the enzyme.

32. The method of claim 31, wherein the subsite is selected from the group consisting of $S_1$, $S_1'$, and $S_2$.

33. The modified subtilisin of claim 9, wherein the modified amino acid is S156.

34. The modified subtilisin of claim 9, wherein the modified amino acid is S166.

35. The method of claim 21, wherein the amino acid replaced with a cysteine is S156.

36. The method of claim 21, wherein the amino acid replaced with a cysteine is S166.

37. The modified subtilisin of claim 1, wherein said thiol side chain consists of $SR^3$, wherein $R^3$ is a substituted or unsubstituted phenyl.

38. The modified subtilisin of claim 1, wherein said thiol side chain consists of —$SR^4$, wherein $R^4$ is a substituted or unsubstituted cyclohexyl.

39. The modified subtilisin of claim 1, wherein said thiol side chain consists of —$SR^5$, wherein $R^5$ is $C_{10}$–$C_{15}$ alkyl.

* * * * *